(12) United States Patent
Pletcher et al.

(10) Patent No.: US 10,873,401 B1
(45) Date of Patent: Dec. 22, 2020

(54) EMPLOYING OPTICAL SIGNALS FOR POWER AND/OR COMMUNICATION

(71) Applicant: Verily Life Sciences LLC, Mountain View, CA (US)

(72) Inventors: Nathan Pletcher, Mountain View, CA (US); Brian Otis, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 16/295,658

(22) Filed: Mar. 7, 2019

Related U.S. Application Data

(63) Continuation of application No. 15/645,486, filed on Jul. 10, 2017, now Pat. No. 10,256,919, which is a
(Continued)

(51) Int. Cl.

| | | |
|---|---|---|
| G02C 7/04 | (2006.01) |
| H04B 10/80 | (2013.01) |
| G06K 7/10 | (2006.01) |
| A61B 5/00 | (2006.01) |
| A61B 5/01 | (2006.01) |

(Continued)

(52) U.S. Cl.
CPC ......... *H04B 10/807* (2013.01); *A61B 5/0017* (2013.01); *A61B 5/01* (2013.01); *A61B 5/14532* (2013.01); *A61B 5/6821* (2013.01); *A61B 5/72* (2013.01); *G02C 7/04* (2013.01); *G02C 11/10* (2013.01); *G06K 7/10158* (2013.01)

(58) Field of Classification Search
CPC .......... G02C 7/04; G02C 11/10; G02C 7/049; G02C 7/047; G02C 7/083

USPC ........................................ 351/159.02, 159.03
See application file for complete search history.

(56) References Cited

U.S. PATENT DOCUMENTS

| | | | |
|---|---|---|---|
| 3,958,560 A | 5/1976 | March |
| 4,014,321 A | 3/1977 | March |
| | (Continued) | |

FOREIGN PATENT DOCUMENTS

| | | | |
|---|---|---|---|
| EP | 0369942 A1 | 5/1990 |
| EP | 686372 A1 | 12/1995 |
| | (Continued) | |

OTHER PUBLICATIONS

Badugu et al., "A Glucose Sensing Contact Lens: A Mon-Invasive Technique for Continuous Physiological Glucose Monitoring", Journal of Fluorescence, Sep. 2003, pp. 371-374, vol. 13, No. 5.
(Continued)

*Primary Examiner* — Hung X Dang
(74) *Attorney, Agent, or Firm* — McDonnell Boehnen Hulbert & Berghoff LLP

(57) ABSTRACT

Apparatus, systems and methods employing contact lens sensors are provided. In some aspects, a contact lens includes a substrate that forms at least a portion of the body of the contact lens; an optical communication device disposed on or within the substrate; and a photodetector disposed on or within the substrate, wherein the photodetector harvests light emitted from a device and generates power from the harvested light. In some aspects, an apparatus comprises a tag having a circuit including: an optical communication device; and a photodetector that harvests light received and generates power from the harvested light. The tag can be disposed on or within a contact lens in various aspects.

20 Claims, 9 Drawing Sheets

Related U.S. Application Data continuation of application No. 14/850,704, filed on Sep. 10, 2015, now Pat. No. 9,735,892, which is a continuation of application No. 13/559,350, filed on Jul. 26, 2012, now Pat. No. 9,158,133.

(51) Int. Cl.
*A61B 5/145* (2006.01)
*G02C 11/00* (2006.01)

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint, Jr. |
| 5,177,165 A | 1/1993 | Valint, Jr. et al. |
| 5,177,168 A | 1/1993 | Baron et al. |
| 5,219,965 A | 6/1993 | Valint, Jr. et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint, Jr. et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint, Jr. et al. |
| 6,087,941 A | 7/2000 | Ferraz |
| 6,131,580 A | 10/2000 | Ratner et al. |
| 6,193,369 B1 | 2/2001 | Valint, Jr. et al. |
| 6,200,626 B1 | 3/2001 | Grobe, III et al. |
| 6,213,604 B1 | 4/2001 | Valint, Jr. et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint, Jr. et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint, Jr. et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Peterson et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,446,341 B2 * | 5/2013 | Amirparviz .......... A61B 5/1455 250/221 |
| 8,827,445 B1 | 9/2014 | Wiser et al. |
| 9,158,133 B1 * | 10/2015 | Pletcher ............... G02C 11/10 |
| 9,735,892 B1 | 8/2017 | Pletcher et al. |
| 10,256,919 B1 | 4/2019 | Pletcher et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |

(56) References Cited

U.S. PATENT DOCUMENTS

| | | |
|---|---|---|
| 2011/0040161 A1 | 2/2011 | Abreu |
| 2011/0055317 A1 | 3/2011 | Vonog et al. |
| 2011/0063556 A1 | 3/2011 | Ahn |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 A1 | 12/2000 |
| EP | 1617757 A1 | 1/2006 |
| EP | 1818008 A1 | 8/2007 |
| EP | 1947501 A2 | 7/2008 |
| EP | 2457122 A1 | 5/2012 |
| WO | 9504609 A1 | 2/1995 |
| WO | 0116641 A1 | 3/2001 |
| WO | 0134312 A1 | 5/2001 |
| WO | 03065876 A2 | 8/2003 |
| WO | 2004060431 A1 | 7/2004 |
| WO | 2004064629 A1 | 8/2004 |
| WO | 2006015315 A2 | 2/2006 |
| WO | 2009094643 A2 | 7/2009 |
| WO | 2010105728 A2 | 9/2010 |
| WO | 2010133317 A1 | 11/2010 |
| WO | 2011011344 A1 | 1/2011 |
| WO | 2011034592 A1 | 3/2011 |
| WO | 2011035228 A1 | 3/2011 |
| WO | 2011035262 A1 | 3/2011 |
| WO | 2011083105 A1 | 7/2011 |
| WO | 2011163080 A1 | 12/2011 |
| WO | 2012035429 A2 | 3/2012 |
| WO | 2012037455 A1 | 3/2012 |
| WO | 2012051167 A1 | 4/2012 |
| WO | 2012051223 A2 | 4/2012 |
| WO | 2012052765 A2 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

"Contact Lenses: Look Into My Eyes," The Economist, Jun. 2, 2011, http://www.economist.com/node/ 187 50624/ print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Ho et al., "Contact Lens With Integrated Inorganic Semiconductor Devices," MEMS 2008. IEEE 21st International Conference on. IEEE, 2008., pp. 403-406.

Holloway, "Microsoft developing electronic contact lens to monitor blood sugar," Gizmag, Jan. 5, 2012, http://www.gizmag.com/microsoft-electronic-diabetic-contact-lens/20987 /, Last accessed Mar. 13, 2012, 5 pages.

Landesmaki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Techno!, 2012, pp. 453-458, vol. 18.

Murdan, "Electro-responsive drug delivery from hydro gels," Journal of Controlled Release, 2003, pp. 1-17, vol. 92.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007, pp. 755-758.

Sensimed Triggerfish, Sensimed Brochure, 2010, 10 pages.

Shin, Yi-Chun et al., "An Inductorless DC-DC Converter for Energy Harvesting With a 1.2! W Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-I to 73970K-8, vol. 7397.

Singh, et al., "Novel Approaches in Formulation and Drug Delivery using Contact Lenses," Journal of Basic and Clinical Pharmacy, May 2011, pp. 87-101, vol. 2, Issue 2.

Stauth et al., "Self-assembled single-crystal silicon circuits on plastic," PNAS, Sep. 19, 2006, pp. 13922-13927, vol. 103, No. 38.

Yao, H. et al. "A contact lens with integrated telecommunication circuit and sensors for wireless and continuous tear ilucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 uA, Addressable Gent Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

Wall, K., "Active contact lens that lets you see like the Terminator patented," Feb. 10, 2012, http://www.patexia.com/feed/active-contactlens-that-lets-you-see-like-the-terminator-patented-2407, Last accessed Mar. 28, 2012, 5 pages.

Parviz, Babak A., "Augmented Reality in a Contact Lens," IEEE Spectrum, Sep. 2009, http://spectrumieee.org/biomedical/bionics/augmented-reality-in-a-contact-lens/0, Last accessed Mar. 14, 2012, 6 pages.

Bionic contact lens 'To project emails before eyes,' http://www.kurzweilai.net/forums/topic/bionic-contact-lens-to-project-emailsbefore-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 157 6-15 89, Materials Research Society.

Brahim, et al., "Polypyrrole-hydrogel composites for the construction of clinically important biosensors," 2002, Biosensors & Bioelectronics, vol. 17, pp. 53-59.

(56) References Cited

OTHER PUBLICATIONS

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthahnol, 2010, vol. 45, No. 5, pp. 457-476.

Selner, et al., "Novel Contact Lens Electrode Array for Multielectrode Electroretinography (meERG)," IEEE, 2011, 2 pages.

Liao, et al., "A 3-uW CMOS Glucose Sensor for Wireless Contact Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

Liao, et al., "A 3uW Wirelessly Powered CMOS Glucose Sensor for an Active Contact Lens," 2011 IEEE International Solid-State Circuits Conference, Session 2, Feb. 21, 2011, 3 pages.

Hurst, "How contact lenses could help save your life," Mail Online, Apr. 19, 2010, http://www.dailymail.co.uk/health/article-1267345/How-contact-lenses-help-save-life.htrnl, Last accessed Jul. 27, 2012.

Loncar, et al., "Design and Fabrication of Silicon Photonic Crystal Optical Waveguides," Journal of Lightwave Technology, Oct. 2000, vol. 18, No. 10, pp. 1402-1411.

Baxter, "Capacitive Sensors," 2000, 17 pages.

Lingley, et al., "A Single-Pixel Wireless Contact Lens Display," Journal of Micromechanics and Microengineering, 2011, 9 pages.

\* cited by examiner

EMPLOYING OPTICAL SIGNALS FOR POWER AND/OR COMMUNICATION

CROSS-REFERENCE TO RELATED APPLICATIONS

This application is a continuation if application Ser. No. 15/645,486, filed Jul. 10, 2017, now U.S. Pat. No. 10,256,919, which is a continuation of application Ser. No. 14/850,704, filed Sep. 10, 2015, now U.S. Pat. No. 9,735,892 which is a continuation of application Ser. No. 13/559,350, filed Jul. 26, 2012 now U.S. Pat. No. 9,158,133. The foregoing applications are incorporated herein by reference.

TECHNICAL FIELD AND SUMMARY

This disclosure generally relates to a contact lens employing optical signals for power and/or communication. In one aspect, a sensing device comprises: one or more sensors configured to sense one or more biological features associated with an eye; a photodetector, wherein the photodetector is configured to harvest ambient light and to generate power from the harvested light; and an optical communication device configured to transmit an optical signal, wherein the optical signal communicates information about the one or more sensed biological features. In another aspect, a method comprises: sensing, by one or more sensors in a sensing device at an eye, one or more biological features associated with the eye; harvesting, by a photodetector in the sensing device, ambient light to generate power for the sensing device; and transmitting, by an optical communication device in the sensing device, an optical signal, wherein the optical signal communicates information about the one or more sensed biological features.

DETAILED DESCRIPTION

Figure 1:
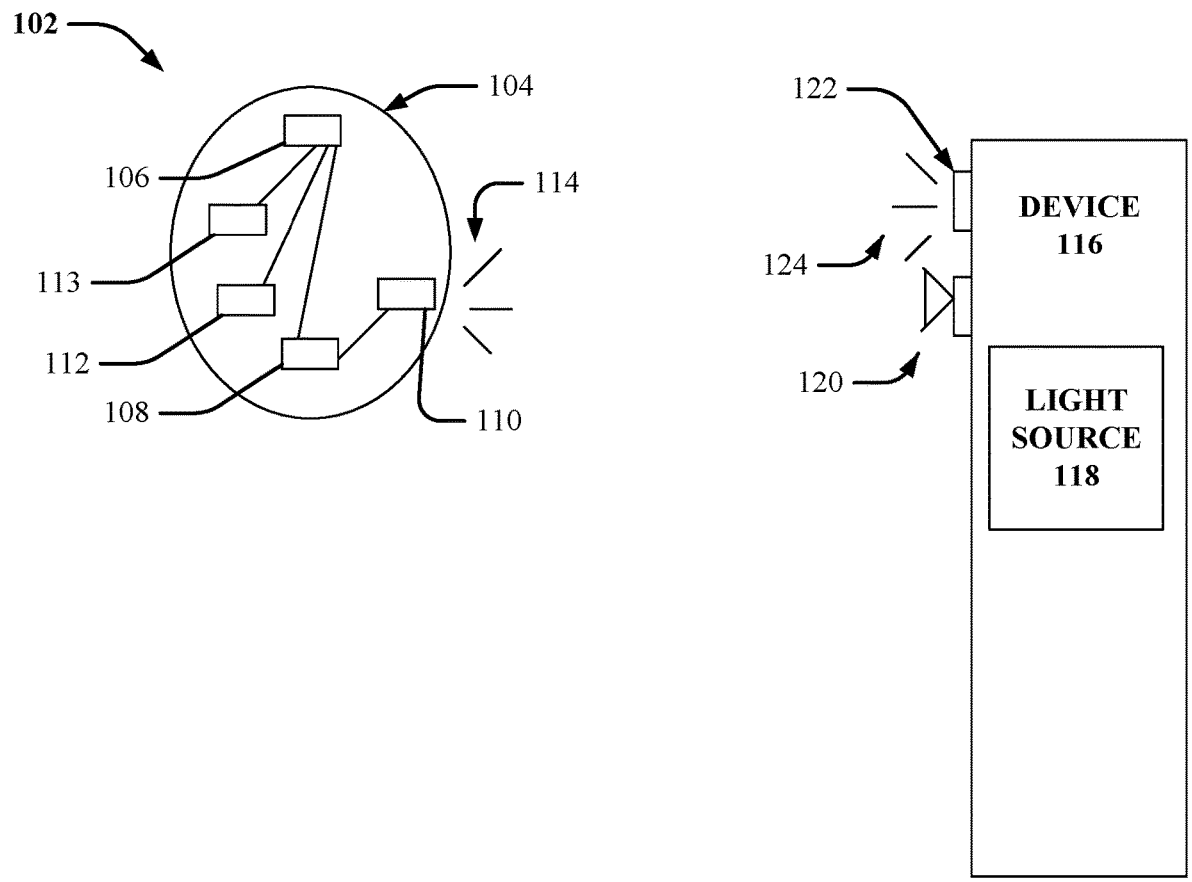
FIGS. 1, 2 and 3 are illustrations of diagrams of exemplary non-limiting systems that facilitate contact lenses employing optical signals for power and/or communication in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

As used in this application, the terms "component," "component," "system," and the like are intended to refer to a computer-related entity, either hardware, software, firmware, a combination of hardware and software, software and/or software in execution. For example, a component can be, but is not limited to being, a process running on a processor, a processor, an object, an executable, a thread of execution, a program, and/or a computer. By way of illustration, both an application running on a computing device and/or the computing device can be a component. One or more components can reside within a process and/or thread of execution and a component can be localized on one computer and/or distributed between two or more computers. In addition, these components can execute from various computer-readable storage media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

The word "exemplary" is used herein to mean serving as an example, instance, or illustration. For the avoidance of doubt, the subject matter disclosed herein is not limited by such examples. In addition, any aspect or design described in this disclosure as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received, or transmitted data.

Active contact lens systems generally do not include an on-board energy source due to space and power limitations on the contact lens. Accordingly, RF harvesting and corresponding backscatter can be used for powering the contact lens and, in some cases, communicating with the contact lens. However, specialized and dedicated RF electronics would typically be required to facilitate RF power and communication; and such electronics can be complex and expensive.

Optical communication is a form of telecommunication that employs light as a transmission medium. Optical signals can be advantageous for enabling power generation and/or communication on a small-scale, such as those areas typically required for active contact lenses. A light transmitter can emit a light signal, which can be received by a light detector.

Micro-fabrication techniques can be employed to provide components that can receive and/or transmit light from or to the contact lens. For example, optical waveguides can be designed and fabricated that incorporate two-dimensional (2-D) photonic crystal geometry for lateral confinement of light, and total internal reflection for vertical confinement. Square, triangular or other suitable photonic crystal lattices can be utilized. In an aspect, a three-dimensional (3-D) finite-difference time-domain (FDTD) can be used to find design parameters of the photonic crystal and to calculate dispersion relations for guided modes in a waveguide structure. In an aspect, the waveguides can be fabricated so as to improve confinement in a particular direction and symmetry properties of the structure. High-resolution fabrication can provide for different types of bends and optical cavities within the waveguides. The optical waveguides can facilitate directing light to and from components of the contact lens, and facilitate mitigation of losses associated with dispersion of light.

Sensors can be employed on the contact lens to facilitate power generation from light. Photodetectors are one such type of sensor that can facilitate power generation. Photodetectors are typically made of a photodiode and circuitry that outputs a current in response to detected light. These types of detectors can harvest light emitted from the light source and generate power from the harvested light.

Optical communication devices (e.g., reflectors, light-emitting diodes (LEDs)) that utilize light can be employed to communicate in response to light received. Communication can be performed by modulation of optical data back to a receiver. For example, a modulating retro-reflector (MRR) system can modulate received light (thereby changing the intensity of the light) and reflect the received light back to a light source. Any number of well-known optical modulation techniques can be employed. Additionally, the small-scale of the MRR system can facilitate on-board power savings up to an order of magnitude over the power consumption of typical RF systems.

Multiple optical transmitters can be situated on the contact lens and multiplex and/or modulate multiple optical signals (e.g., using different sources as well as different colors, or wavelength frequencies) in order to enhance encoding of data (e.g., data sensed on the contact lens). For example, optical signals can be modulated with data whereby the modulation type is a function of the data being transmitted.

Further, an optical add-drop multiplexing device can multiplex different sources of light for transmission from the contact lens. In this case, more than one modulated light signal is transmitted on the same carrier, or channel. Different channels can be encoded with the same or different data, and multiplexed prior to transmission.

Apparatus, systems and methods disclosed herein relate to contact lenses employing optical signals for power and/or communication. In one or more aspects, a contact lens can include: a substrate that forms at least a portion of the body of the contact lens; an optical communication device disposed on or within the substrate; and a photodetector disposed on or within the substrate, wherein the photodetector harvests light emitted from a device and generates power from the harvested light, wherein the device is located external to the contact lens.

In one or more aspects, the disclosed subject matter relates to a system. The system can include: a contact lens and a device. The contact lens can include: a substrate; and a circuit disposed on or within the substrate. The circuit can include: one or more sensors that sense a feature of a wearer of the contact lens; a communication component that outputs information indicative of the sensed feature from the contact lens; a processor that processes the information indicative of the sensed feature; and one or more light sensors that sense light and power at least one of the component or the processor, based, at least, on the sensed light, wherein the component outputs the information in response to the sensed light. The device can have a transmitter that emits the light sensed by the one or more light sensors.

One or more aspects of the apparatus, systems and/or methods described herein can advantageously employ optical signals for power and/or communication on a contact lens. Accordingly, the aspects can reduce the space typically employed for components on the contact lens that utilize RF components for power and/or communication.

Figure 2:
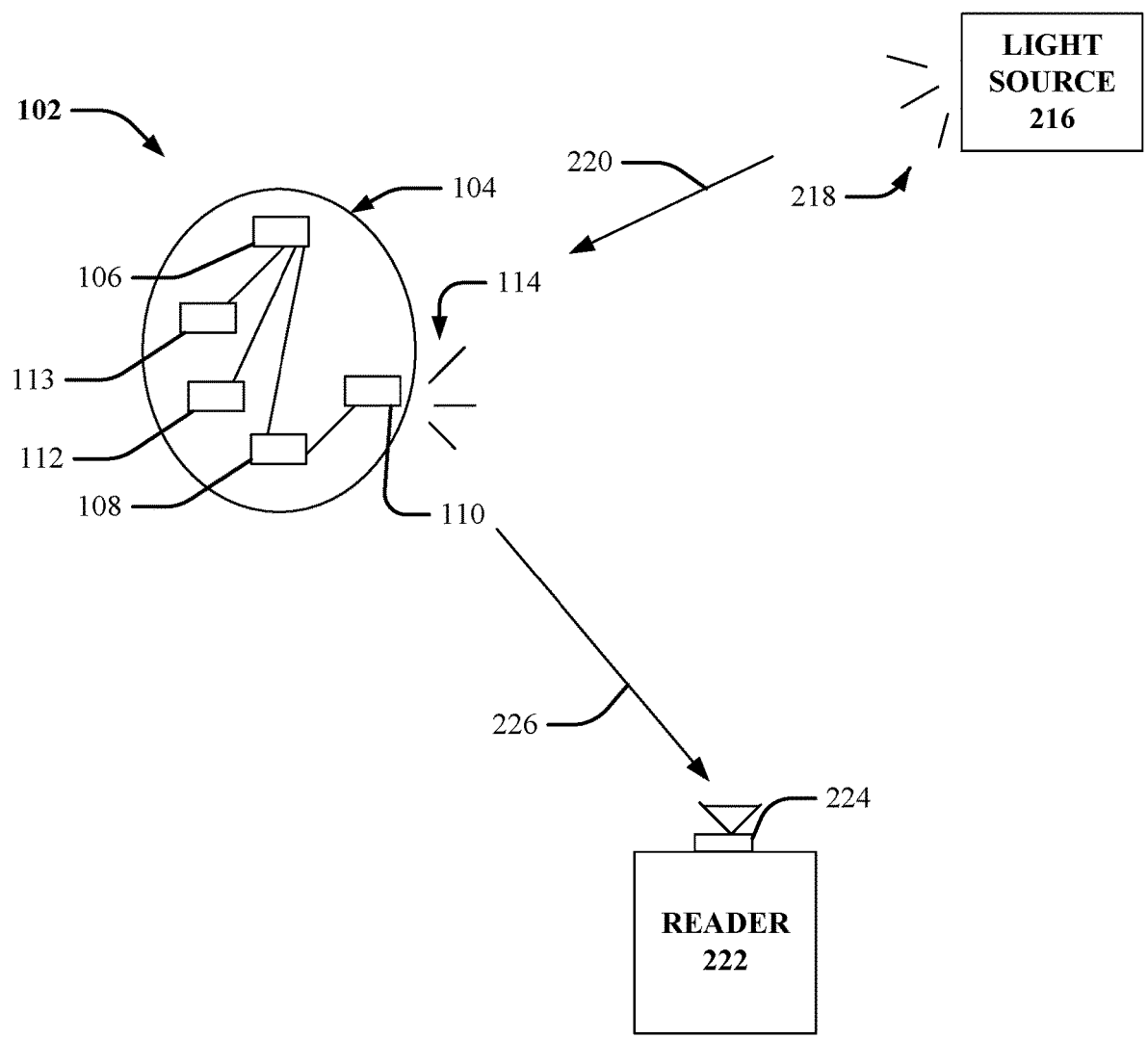
Figure 3:
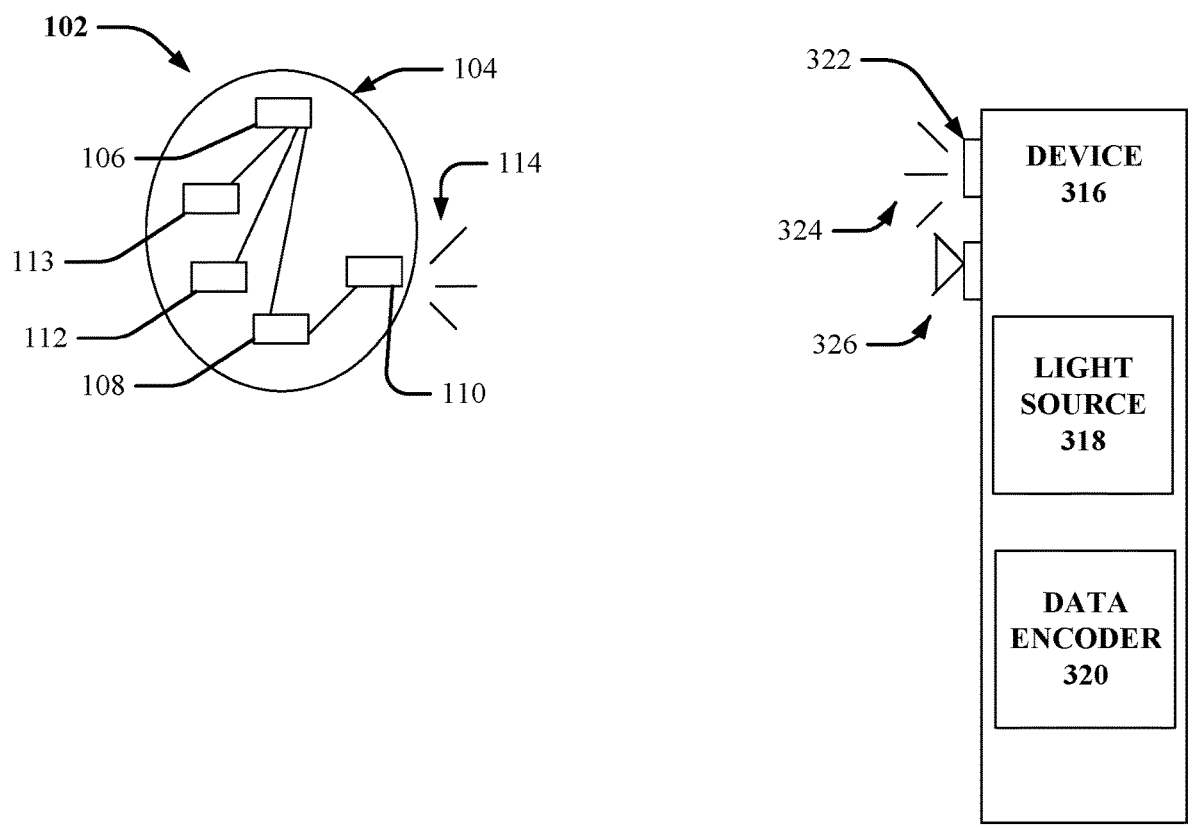

FIGS. 1, 2 and 3 are illustrations of diagrams of exemplary non-limiting systems that facilitate contact lenses employing optical signals for power and/or communication in accordance with aspects described herein.

Turning first to FIG. 1, system 100 can include a contact lens 102 and a device 116. The contact lens 102 can include a substrate 104, a photodetector 106, a sensor 108, an optical communication device 110, a microprocessor 112 and/or memory 113. In various aspects, one or more of the photodetector 106, sensor 108, optical communication device 110, microprocessor 112 and/or memory 113 can be optically, electrically and/or communicatively coupled to one another to perform one or more of the functions (e.g., generating power, sensing, communication) of the contact lens 102.

In some aspects, the substrate 104 can form at least a portion of the body of the contact lens 102. The substrate 104 can be flexible or semi-rigid in various aspects. Further, the substrate 104 can be transparent or translucent in various aspects.

In various aspects, the photodetector 106 can be any number of components that can detect and receive light. By way of example, but not limitation, the photodetector 106 can be a photovoltaic cell or a solar cell.

The photodetector 106 can be disposed on or within the substrate 104 in various aspects. For example, in some aspects, the photodetector 106 can be encapsulated within the substrate 104 while, in other aspects, the photodetector 106 is disposed on the surface of the substrate 104 or embedded within the surface of the substrate 104.

The photodetector 106 can harvest optical signals emitted from the device 116 and generate power from the harvested optical signals. For example, the photovoltaic cells or solar cells can receive the optical signals wirelessly. The received optical signals can be harvested, and power can be subsequently generated for use by the contact lens 102.

In various aspects, the photodetector 106 can detect modulated optical signals from the device 116 to receive data from the device 116. For example, the optical signals can be modulated with data in some embodiments. In these embodiments, the contact lens 102 can include circuitry that demodulates the optical signal. Upon receipt of the modulated optical signals, the contact lens 102 can demodulate the received optical signal and extract the data with which the optical signal is modulated. The data with which the optical signal is modulated can include, but is not limited to, data for adjustment of various parameters of the components of the contact lens 102, data to be stored in the memory 113 or the like.

In various aspects, irrespective of whether the optical signal is modulated with data, the optical signal 124 received can be employed, power can be generated from the receipt of the optical signal, and the power can be employed to power the sensor 108 of the contact lens 102.

The sensor 108 can sense one or more features of the wearer of the contact lens 102. For example, the sensor 108 can sense any number of biological features of the wearer of the contact lens 102 including, but not limited to, glucose, lactate or urea levels, internal body temperature and/or blood alcohol content of the wearer of the contact lens 102 as described in further detail below.

For example, in some aspects, the sensor 108 can detect fluid on the substrate 104 from the eye of the wearer of the contact lens 102. The sensor 108 can sense level of glucose, lactate and/or urea in the fluid. In some embodiments, the contact lens 102 can include circuitry for evaluating the level of the substance in the fluid. In some embodiments, the contact lens 102 can include circuitry for outputting the sensed information to a reader. In either aspect, the level of the biological matter can be compared to a threshold. A determination can be made as to whether the level is too high or too low based on the level detected.

In another aspect, retinal analysis of a user can be performed and an optical signal transmitted in response to an authentication request.

As another example, the fluid on the substrate 104 can be a particular temperature. The temperature of the fluid can be indicative of the internal temperature of the wearer of the contact lens 102. The sensor 108 can be a temperature sensor that can sense the temperature of the fluid. For example, in some embodiments, the sensor 108 can be a resistance thermometer that detects the temperature based on an increase in resistance (which occurs with a rise in temperature) or a decrease in resistance (which occurs with a decrease in temperature). The sensor 108 can be employed in connection with a thermistor in some embodiments. As another example, the sensor 108 can sense a blood alcohol content of the wearer of the contact lens 102. In particular, the sensor 108 can detect the fluid incident on the substrate 104. For example, the tear film on the eye can be incident on the contact lens 102. The alcohol concentration in the tear film can be sensed by sensor 108.

In some aspects, the sensor 108 can sense one or more features in an environment outside of the wearer of the contact lens 102. For example, the sensor 108 can sense any number of biological, chemical and/or microbiological features in an environment including, but not limited to, levels of hazardous materials, levels of allergens, the presence of various organisms or species or the like. For example, in various embodiments, the sensor 108 can sense a level of one or more different allergens (e.g., tree or grass pollen, pet dander, dust mite excretions) in the environment.

While the aspect shown illustrates a single sensor 108, in various aspects, any number of sensors can be disposed on or within the substrate 104. Further, the one or more sensors can be disposed in any number of configurations for sensing the features described herein. By way of example, but not limitation, the one or more sensors can be disposed in a circular or semi-circular configuration around the periphery of the contact lens 102.

The optical communication device 110 can be disposed on or within the substrate 104. In various aspects, the optical communication device 110 can be or include a light-emitting diode (LED) or a reflector. The LED and/or reflector can modulate in one or more different patterns to communicate specific information about the sensed features to a reader or to the device 116. The reader or device 116 can be configured with components that are programmed to correlate particular modulated patterns with specific information and, as such, can determine the information based upon receipt of the pattern.

In various aspects, the contact lens 102 can include a communication device (not shown) that can output information (e.g., sensed features, information associated with sensed biological or chemical materials, information associated with internal temperature and/or blood alcohol concentration in the tear film of the eye) from the contact lens 102. In some aspects, the contact lens 102 can include the communication device in addition to or in lieu of the optical communication device 110. The communication device can be optically-powered in various aspects.

The microprocessor 112 can include logic circuitry that can cause one or more components of the contact lens 102 to perform one or more functions and/or that can perform one or more functions of the contact lens 102. For example, the microprocessor 112 can cause one or more of the power generation, sensing and/or communication functions to be performed via the contact lens 102. In some aspects, the microprocessor 112 can employ computer-executable instructions and/or information stored in the memory 113 to perform the functions (or to cause the functions to be performed).

The memory 113 can include a computer-readable storage medium storing computer-executable instructions and/or information for performing the functions described in this disclosure with reference to the contact lens 102. In various aspects, the memory 113 can store information including, but not limited to, the sensed features (or information indicative thereof) or data received via the optical signal (e.g., data with which the optical signal is modulated).

Accordingly, in summary, in some aspects, the photodetector 106 can receive an optical signal, the sensor 108 can be powered by power generated from the optical signal and the sensor 108 can output the sensed information. The optical communication device 110 can modulate in a particular pattern in a manner dictated by the output sensed information. As such, the modulation can be according to the particular sensed information sensed by the sensor 108. The device 116 can receive the modulated signal generated by the optical communication device 110 and determine the information sensed by the sensor 108 based on the modulated signal received.

Although not shown, in various aspects, the contact lens 102 can include structure and/or functionality to convert the optical signal to an electrical signal. For example, in some aspects, the contact lens 102 can include a photodiode that converts optical signals to electrical current or voltage. The electrical signal can be employed to power one or more components of the contact lens 102 in various aspects.

Although also not shown, in various aspects, the contact lens 102 can include structure and/or functionality to receive and/or decode infrared (IR) light.

Turning now to the device 116, in lieu of or in addition to receiving a modulated signal, in some aspects, the device 116 can include a light source 118 that can generate light. For example, the device 116 can generate light, in particular, or an optical signal, generally (e.g., a flash of a camera). The optical signal 124 can be emitted from an optical-signal emitting component 122 of the device 116 in various aspects. In some aspects, the optical-signal emitting component 122 can be a component that generates a flash in a camera, for example.

In some aspects, the device 116 can be positioned within a particular proximity to the contact lens 102 prior to generating the optical signal such that the optical signal 124 emitted from the device is received by the contact lens 102. For example, the device 116 can be within one to two feet of the contact lens 102 when the optical signal is generated. As such, the photovoltaic cells and/or solar cells can receive the optical signal and convert the signal to power the components (e.g., the one or more sensors).

In some aspects, as described above, the device 116 can also be adapted to receive the modulated signal from the optical communication device 110. For example, the device 116 can receive the modulated signal at optical-signal receiving component 120 of the device 116. Optical-signal receiving component 120 can be any number of different types of receivers that can receive optical signals. The device 116 can determine the information received based on the modulated signal generated by the optical communication device 110.

In various aspects, the device 116 can be or include any of a number of different devices having hardware and/or software that transmits and/or receives an optical signal. In some aspects, the hardware that generates and/or transmits the optical signal can be general purpose hardware that currently exists on a mobile phone or camera. For example, in some aspects, the hardware can be hardware that generates a flash that is emitted from a camera with a flash feature or from a mobile phone (or other device) having a camera with a flash feature. In these aspects, the flash feature can function as an optical transmitter while the camera lens can function as an optical receiver.

Turning now to FIG. 2, another system that facilitates contact lenses employing optical signals for power and/or communication is shown. System 200 can include contact lens 102, a light source 216 and a reader 222.

The light source 216 can be any number of sources that can generate light (or optical signals generally). By way of example, but not limitation, the light source 216 can be the sun, a source of low-level background light or a device having an optical-signal emitting component such as one above embodiment of device 116 described with reference to FIG. 1. The light source 216 can emit an optical signal 218, 220 that can be received by the contact lens 102. For example, the optical signal 218, 220 can be received by the photodetector 106 as described above with reference to FIG. 1.

The reader 222 can be adapted to receive the modulated signal from the optical communication device 110. For example, the reader 222 can receive the modulated signal at optical-signal receiving component 224 of the reader 222. Optical-signal receiving component 224 can be any number of different types of receivers that can receive and/or sense optical signals. In some aspects, for example, the optical-signal receiving component 224 can include an optical demodulator that is configured to demodulate the modulated signal. The reader 222 can determine the information received based on the pattern with which the signal is modulated by the optical communication device 110.

In some aspects, the contact lens can include the structure and/or function described with reference to FIG. 1. In some aspects, the contact lens 102 can receive optical signal 218, 220 emitted from light source 216 and can output an optical signal 114, 226 to reader 222. For example, the optical communication device 110 can output the optical signal 114, 226 to the reader 222 in response to the output from the sensor 108. The sensor 108 can be powered optically via the optical signal 218, 220 received from the light source 216 as described with reference to FIG. 1.

Accordingly, in various aspects, the contact lens 102 can receive an optical signal 218, 220 from a first source (e.g., light source 216) and output an optical signal 114, 226 to a second source (e.g., reader 222).

Turning now to FIG. 3, another system that facilitates contact lenses employing optical signals for power and/or communication is shown. System 300 can include contact lens 102 and device 316.

The device 316 can be any suitable device that can encode an optical signal 324 with data, and output the optical signal 324. In some aspects, the device 316 can include a data encoder 320 that can encode the optical signal 324, and a light source 318 that can emit the optical signal 324 encoded with the data.

In various aspects, the optical signal 324 can be encoded with data at a rate high enough to avoid detection by the human eye and/or brain. For example, in some aspects, the optical signal 324 can be encoded with data at a rate of 100 bits per second (bps) or greater.

In various aspects, the data can include instructions or information for storage in the memory 113. For example, the data can include instructions for particular features to be sensed by the sensor 108.

The optical signal 324 can be output from the component 322 in some aspects. The optical signal 324 can be received by the contact lens 102. For example, the optical signal 218, 220 can be received by the photodetector 106.

The component 326 can be adapted to receive the modulated signal from the optical communication device 110. Component 326 can be any number of different types of receivers that can receive and/or sense optical signals. The component 326 can determine the information received based on the modulated signal generated by the optical communication device 110. In various aspects, the component 326 can be or include any of a number of different devices having hardware and/or software that transmits and receives an optical signal.

In various aspects, the contact lens can include the structure and/or function described with reference to FIG. 1. In some aspects, the contact lens 102 can receive optical signal 218, 220 emitted from device 316 and can output an optical signal 114 to the device 316. The optical signal 114 can be output from the optical communication device 110 in some aspects. The optical communication device 110 can output the optical signal 114 to the device 316 in response to the output from the sensor 108. The sensor 108 can be powered optically via the optical signal 324 received from the device 316.

While not shown, in other aspects, the systems described herein can include those having contact lens 102, a reader (e.g., reader 222) and/or any device able to emit light (or an optical signal generally).

While not shown, the contact lens can include structure and/or functionality for multi-modal operation. In some aspects, multi-modal operation can mean operating intermittently between RF and optical power modes and/or RF and optical communication modes. For example, in some aspects, the contact lens can employ RF-based power and/or communication and, in other instances, the contact lens can employ optical-based power and/or communication. As another example, optical power and RF communication can be employed. For example, in some aspects, the contact lens can harvest optical energy to power the optical communication device on the contact lens, and harvest RF energy to power an RF device on the contact lens. For example, an RF device can communicate via RF reflection, or backscatter.

Figure 4:
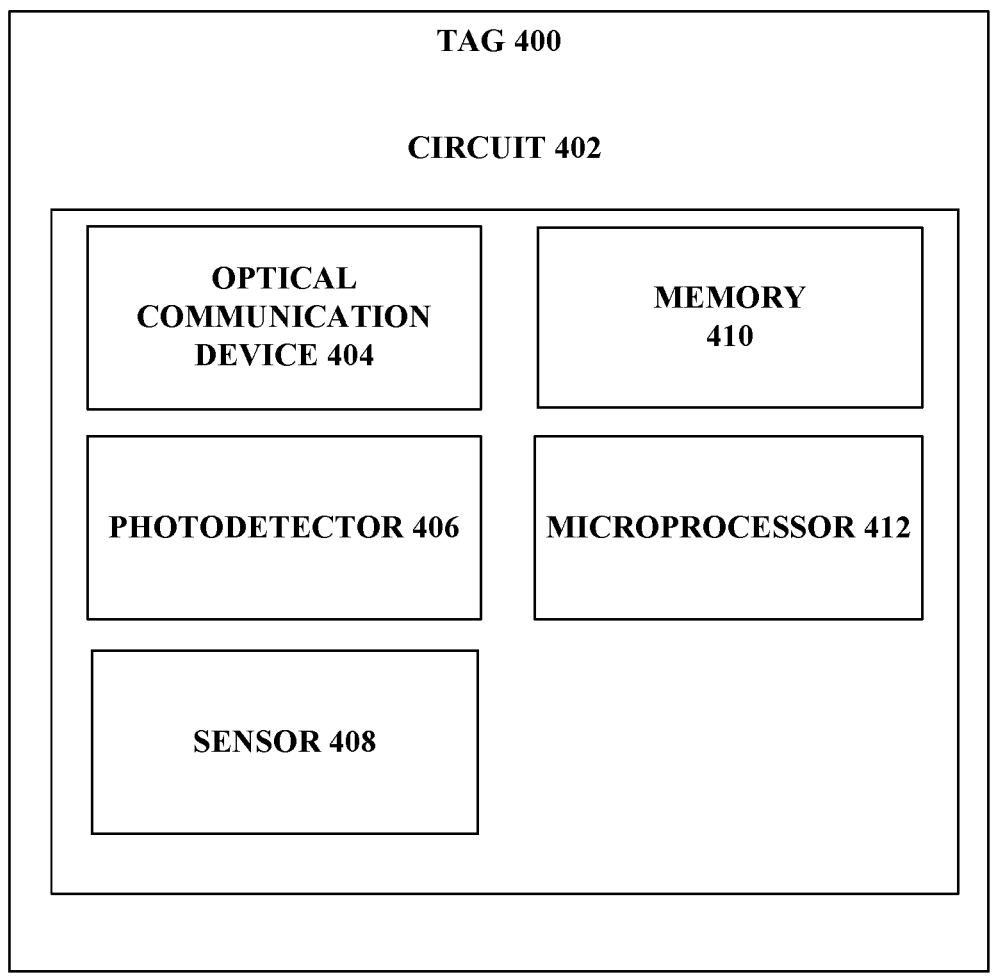
FIG. 4 is an illustration of a block diagram of a tag for a contact lens facilitating optical communication in accordance with aspects described herein.

FIG. 4 is an illustration of a block diagram of a tag for a contact lens facilitating optical communication in accordance with aspects described herein. The tag 400 can be disposed on or within the contact lens in various aspects.

The tag 400 can include or be associated with a circuit 402 disposed on or within the tag 400. In some aspects, the circuit 402 can include an optical communication device 404, a photodetector 406, a sensor 408, a memory 410 and/or a microprocessor 412. In various aspects, the optical communication device 404, photodetector 406, sensor 408, memory 410 and/or microprocessor 412 can be optically, electrically and/or communicatively coupled to one another to perform one or more functions of the tag 400. As such, in some aspects, the tag 400 can be configured to have a level of porosity such that fluids incident on the contact lens can be detected and sensing can be performed by the sensor 408. In some aspects, the tag 400 can be transparent or translucent such that the photodetector 406 can receive light for power generation.

In some aspects, the tag 400 can include information identifying the wearer of the contact lens, information stored and/or detailing features of the wearer of the contact lens or the like.

In some aspects, the tag 400 can be associated with an item (e.g., item of merchandise) and/or can be interrogated by a device (e.g., device 116, device 316, reader 222) for merchandising and/or inventory purposes.

For example, in some aspects, a light source can be associated with or coupled to an item of merchandise. The optical signal can be received by the photodetector 406 to power the components of the tag 400, and the tag 400 can output information via the optical communication device 404. The information output by the tag 400 can be communicated via modulation of the optical communication device 404 as described in one or more of the embodiments.

In some aspects, the light source associated with or coupled to the item of merchandise can transmit information about the item to the tag 400 (e.g., by modulating the optical signal with data about the merchandise). For example, the tag 400 can receive information detailing electronic coupons, pricing, warranty information or the like. The information can be received by and/or stored at the memory 410 of the tag 400.

In some aspects, an interrogator (e.g., device 116, device 316, reader 222) at a point of sale can output an optical signal that can cause the tag 400 to responsively output information related to the merchandise. For example, the tag 400 can respond with information indicative of an electronic coupon for the item of merchandise. For example, the interrogator can be operated by a cashier or other point of sale personnel to cause the tag 400 to output an optical signal detailing the terms of the coupon (in response to the tag 400 of the contact lens receiving an optical signal from the interrogator).

In various aspects, the components of the circuit 402 can include the structure and/or functionality of the corresponding components of the contact lens 102 described with reference to FIG. 1. For example, the photodetector 406 can include the structure and/or functionality of photodetector 106 described with reference to FIG. 1.

Figure 5:
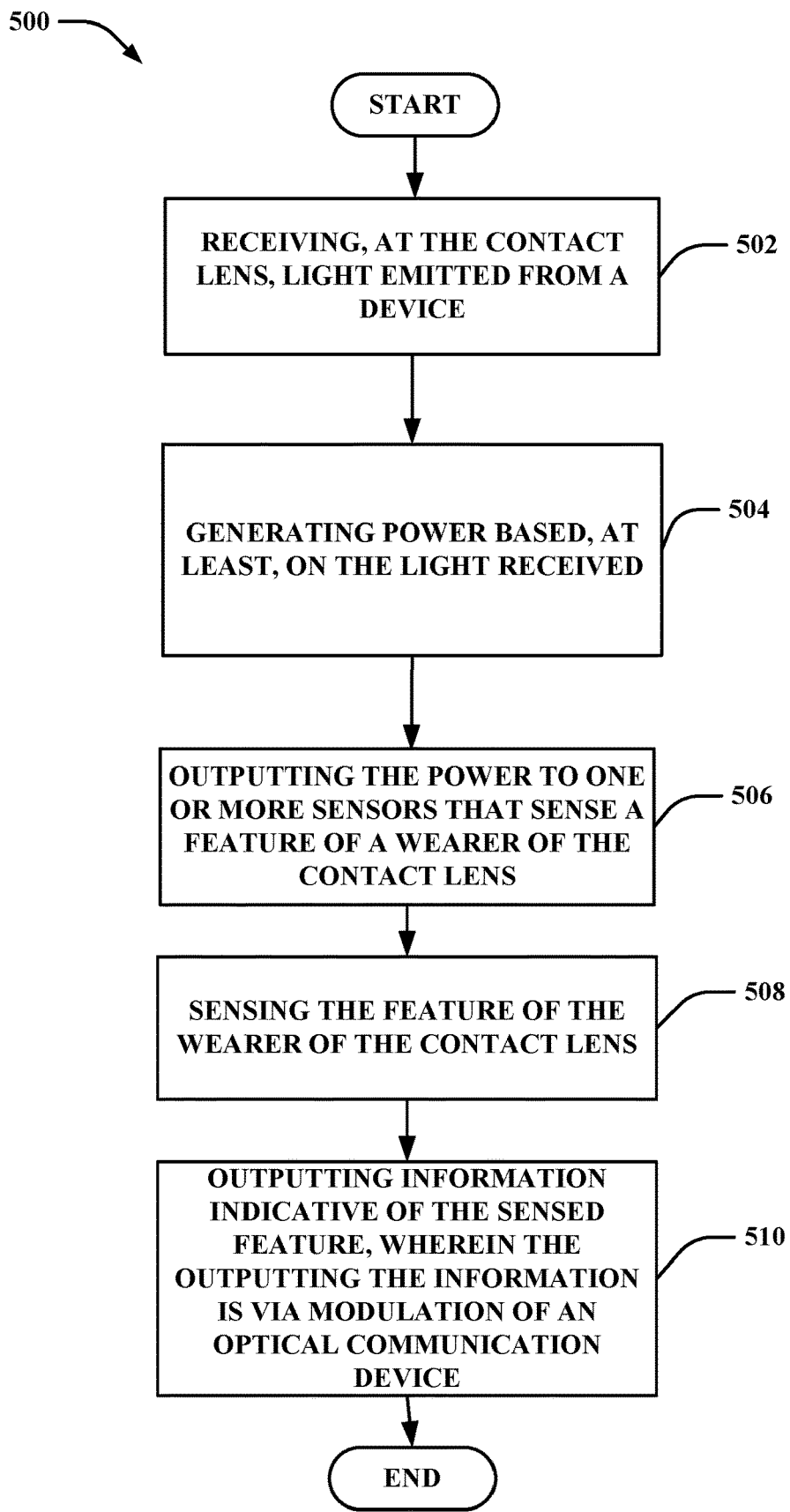
FIGS. 5, 6 and 7 are exemplary flow diagrams of methods that facilitate contact lenses employing optical signals for power and/or communication in accordance with aspects described herein.
Figure 6:
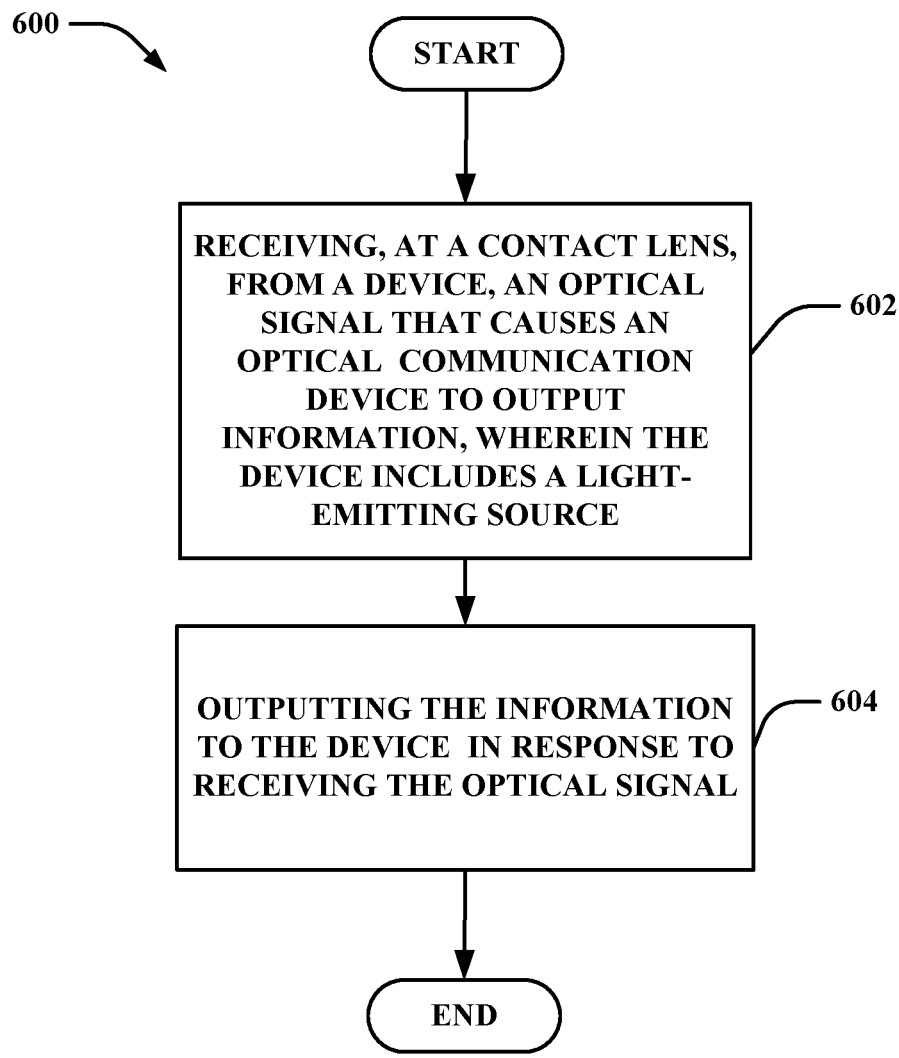
Figure 7:
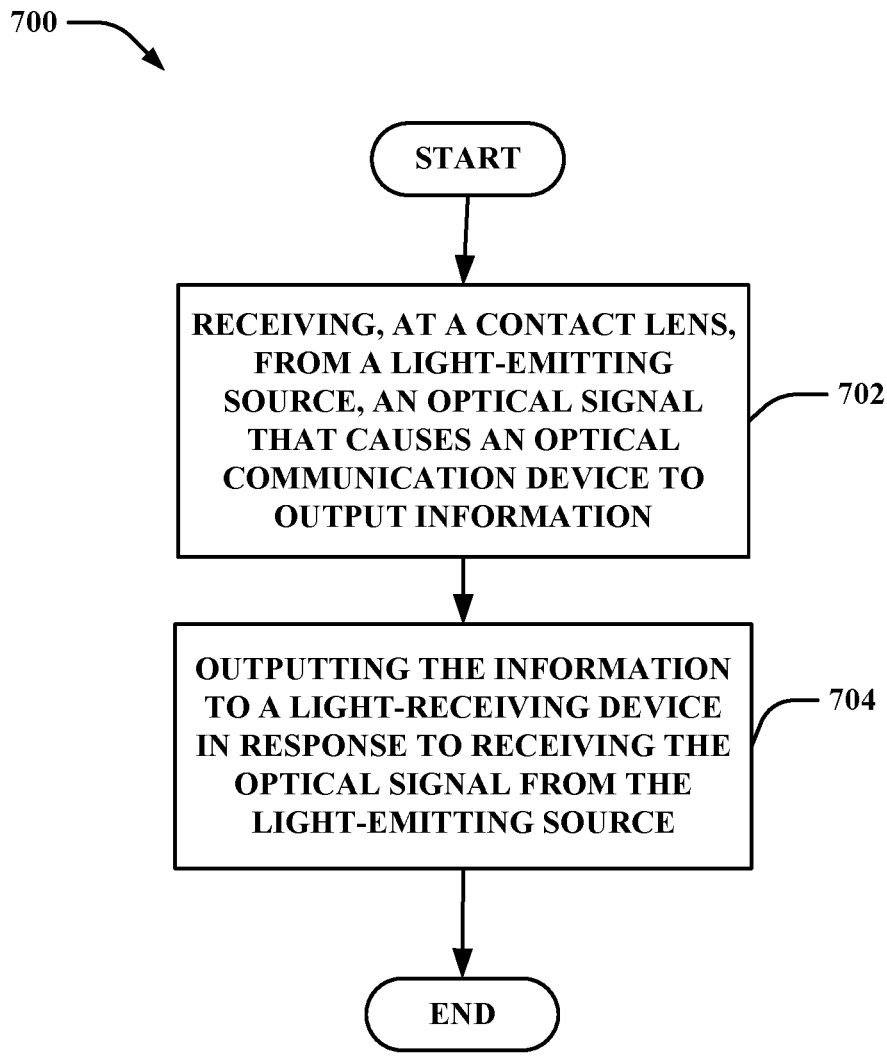

FIGS. 5, 6 and 7 are exemplary flow diagrams of methods that facilitate contact lenses employing optical signals for power and/or communication in accordance with aspects described herein.

Turning first to FIG. 5, at 502, method 500 can include receiving, at the contact lens, light (or an optical signal, generally) emitted from a device (e.g., using the contact lens 102 or the photodetector 106).

In various aspects, the optical signal can be of a wavelength that is invisible or visible to the human eye. For example, the light can be invisible (e.g., IR light) or other light that is invisible to the human eye but that is detectable by the photodetector or other detector (not shown) on the contact lens 102. For example, while not shown, the systems described herein can include those having a device able to emit IR light signals and a contact lens able to receive and decode IR light signals. The device can include circuitry (e.g., IR transmitter, LED) to emit pulses of IR light. The contact lens can include a receiver that can receive and decode the IR light. The microprocessor of the contact lens can decode data encoded in the IR light in some aspects. In these aspects, the contact lens can perform one or more functions based on the decoded data.

As another example, the light received could be visible light (e.g., a flash from a camera). As another example, the light can be low-level background light or ambient light.

As another example, the light can be modulated with data. The rate at which the light is modulated with the data can be approximately 100 bits per second (bps) or greater. In various aspects, the data with which the light is modulated can include information that can be stored at the contact lens. In various aspects, the data with which the light is modulated can include information that can be employed by the contact lens for one or more functions. For example, the data can be information identifying features for sensing by the sensor of the contact lens and/or information identifying a query for information (e.g., biographical information) to be output from the contact lens.

At 504, method 500 can include generating power based, at least, on the light received (e.g., using the photodetector 106). In various aspects, the power can be harvested by the photodetector and employed to power the sensor on the contact lens. As such, an optical signal can be employed for powering the contact lens.

At 506, method 500 can include outputting the power to one or more sensors that sense a feature of a wearer of the contact lens (e.g., using the photodetector 106).

At 508, method 500 can include sensing the feature of the wearer of the contact lens (e.g., using the sensor 108). The feature can include, but is not limited to, a biological and/or chemical feature of the wearer of the contact lens. In some aspects, although not shown, the method 500 can include sensing a feature of an environment outside of a wearer of the contact lens.

For example, the sensor 108 can sense any number of biological features of the wearer of the contact lens including, but not limited to, glucose, lactate or urea levels, internal body temperature and/or blood alcohol content of the wearer of the contact lens as described in further detail below.

For example, in some aspects, the sensor 108 can detect a fluid on the contact lens output from the eye of the wearer of the contact lens. The sensor 108 can sense a level of glucose, lactate and/or urea in the fluid. In some embodiments, the contact lens can include circuitry for evaluating the level of the substance in the fluid. In some embodiments, the contact lens can include circuitry for outputting the sensed information to a reader. In either aspect, the level of the biological matter can be compared to a threshold. A determination can be made as to whether the level is too high or too low based on the level detected.

As another example, the fluid on the contact lens can be a particular temperature. The temperature of the fluid can be indicative of the internal temperature of the wearer of the contact lens. The sensor 108 can be a temperature sensor that can sense the temperature of the fluid. For example, in some embodiments, the sensor 108 can be a resistance thermometer that detects the temperature based on an increase in resistance (which occurs with a rise in temperature) or a decrease in resistance (which occurs with a decrease in temperature). The sensor 108 can be employed in connection with a thermistor in some embodiments. As another example, the sensor 108 can sense a blood alcohol content of the wearer of the contact lens. In particular, the sensor 108 can detect the fluid incident on the contact lens. For example, the tear film of the eye can be incident on the contact lens. The alcohol concentration in the tear film can be sensed by sensor 108.

In some aspects, the sensor 108 can sense one or more features in an environment outside of the wearer of the contact lens. For example, the sensor 108 can sense any number of biological, chemical and/or microbiological features in an environment including, but not limited to, levels of hazardous materials, levels of allergens, the presence of various organisms or species or the like. For example, in various embodiments, the sensor 108 can sense a level of one or more different allergens (e.g., tree or grass pollen, pet dander, dust mite excretions) in the environment. At 510, method 500 can include outputting information indicative of the sensed feature (e.g., using the optical communication device 110). In various aspects, the information can be output from the optical communication device via modulation of the optical communication device. For example, the manner in which the optical communication device is modulated can communicate the details of the information sensed.

Turning now to FIG. 6, at 602, method 600 can include receiving, at a contact lens, from a device, an optical signal that causes an optical communication device to output information (e.g., using the photodetector 106 of the contact lens 102). In some aspects, the device can include a light-emitting source.

At 604, method 600 can include outputting the information to the device (e.g., using the optical communication device 110 of the contact lens 102).

Turning now to FIG. 7, at 702, method 700 can include receiving, at a contact lens, from a light-emitting source, an optical signal that causes an optical communication device to output information (e.g., using the photodetector 106 of the contact lens 102).

In various aspects, the light-emitting source can be a device that emits optical signals. For example, the light-emitting source can be a camera having a component that generates a flash of light. In some aspects, the light-emitting source can be a source of ambient light (e.g., sun) or a source of low-level background light. In some aspects, the light-emitting source can also include structure for modulating the light output with data. As such, the light emitted can include data.

At 704, method 700 can include outputting the information to a light-receiving device (e.g., using the optical communication device 110 of the contact lens 102). In various aspects, the light-receiving device can be a device that receives and reads optical signals. In some aspects, the light-emitting source is distinct from the light-receiving device. As such, the contact lens can receive an optical signal from a first source and emit optical signals to a second source.

Exemplary Networked and Distributed Environments

Figure 8:
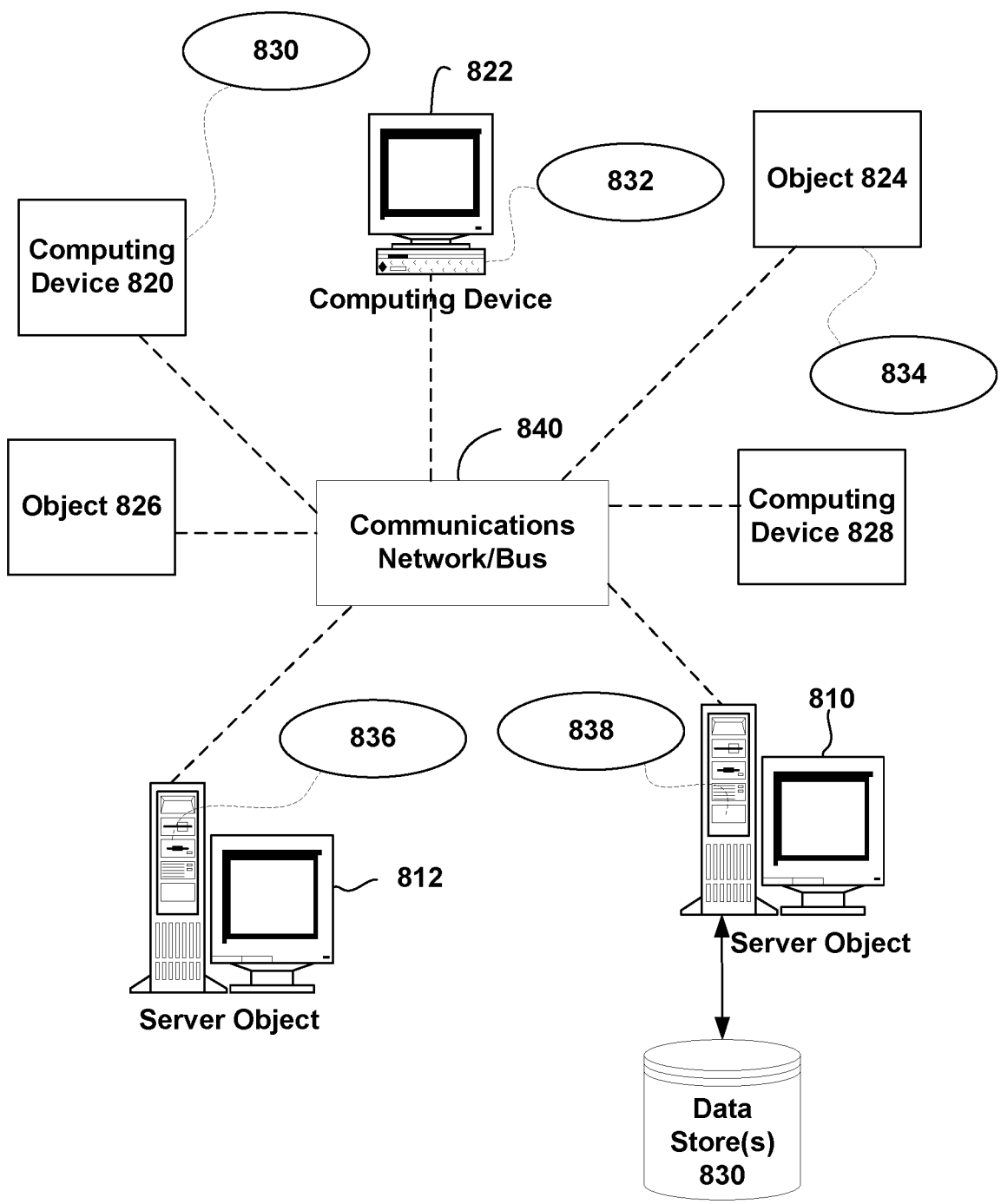
FIG. 8 is an illustration of a schematic diagram of an exemplary networked or distributed computing environment with which one or more aspects described herein can be associated.

FIG. 8 provides a schematic diagram of an exemplary networked or distributed computing environment with which one or more aspects described in this disclosure can be associated. The distributed computing environment includes computing objects 810, 812, etc. and computing objects or devices 820, 822, 824, 826, 828, etc., which can include programs, methods, data stores, programmable logic, etc., as represented by applications 830, 832, 834, 836, 838. It can be appreciated that computing objects 810, 812, etc. and computing objects or devices 820, 822, 824, 826, 828, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 810, 812, etc. and computing objects or devices 820, 822, 824, 826, 828, etc. can communicate with one or more other computing objects 810, 812, etc. and computing objects or devices 820, 822, 824, 826, 828, etc. by way of the communications network 840, either directly or indirectly. Even though illustrated as a single element in FIG. 8, network 840 can include other computing objects and computing devices that provide services to the system of FIG. 8, and/or can represent multiple interconnected networks, which are not shown.

In a network environment in which the communications network/bus 840 can be the Internet, the computing objects 810, 812, etc. can be Web servers, file servers, media servers, etc. with which the client computing objects or devices 820, 822, 824, 826, 828, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or reader described herein. In various aspects, the data store can include or be included within, any of the memory described herein, any of the contact lenses described herein and/or the RF reader described herein. In various aspects, the data store can be any repository for storing information transmitted to or received from the contact lens.

Figure 9:
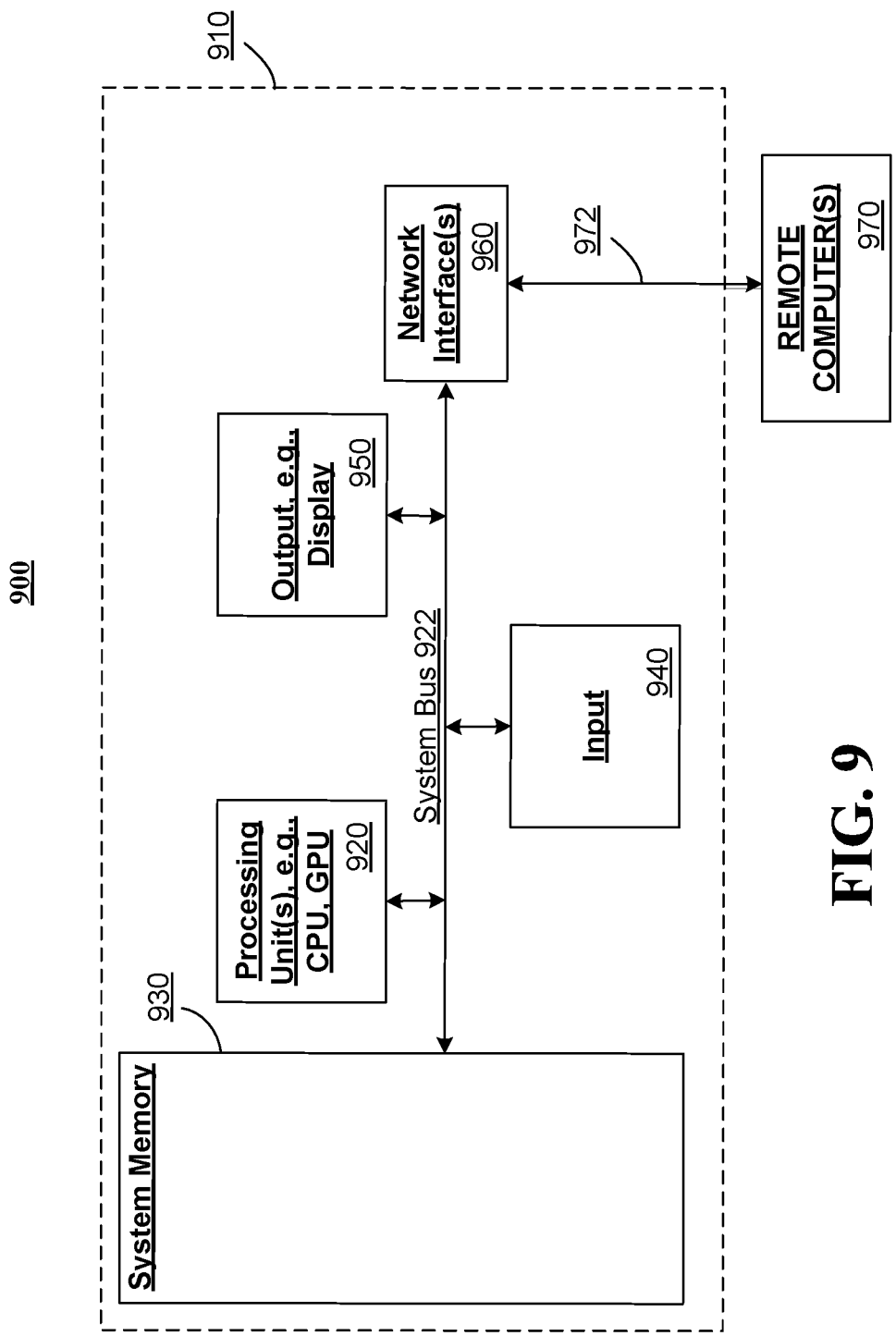
FIG. 9 is an illustration of a schematic diagram of an exemplary computing environment with which one or more aspects described herein can be associated.

FIG. 9 illustrates an example of a suitable computing system environment 900 in which one or aspects of the aspects described in this disclosure can be implemented. Components of computer 910 can include, but are not limited to, a processing unit 920, a system memory 930, and a system bus 922 that couples various system components including the system memory to the processing unit 920.

Computer 910 typically includes a variety of computer readable media and can be any available media that can be accessed by computer 910. The system memory 930 can include computer storage media in the form of volatile and/or nonvolatile memory such as read only memory (ROM) and/or random access memory (RAM). By way of example, and not limitation, memory 930 can also include an operating system, application programs, other program components, and program data.

A user can enter commands and information into the computer 910 through input devices 940 (e.g., keyboard, keypad, a pointing device, a mouse, stylus, touchpad, touch screen, motion detector, camera, microphone or any other device that allows the user to interact with the computer 910). A monitor or other type of display device can be also connected to the system bus 922 via an interface, such as output interface 950. In addition to a monitor, computers can also include other peripheral output devices such as speakers and a printer, which can be connected through output interface 950.

The computer 910 can operate in a networked or distributed environment using logical connections to one or more other remote computers, such as remote computer 980. The remote computer 980 can be a personal computer, a server, a router, a network PC, a peer device or other common network node, or any other remote media consumption or transmission device, and can include any or all of the elements described above relative to the computer 910. The logical connections depicted in FIG. 9 include a network 982, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A sensing device, comprising:
   one or more sensors configured to sense one or more biological features associated with an eye;
   a photodetector, wherein the photodetector is configured to harvest ambient light and to generate power from the harvested light; and
   an optical communication device configured to transmit an optical signal, wherein the optical signal communicates information about the one or more sensed biological features.

2. The sensing device of claim 1, wherein the photodetector comprises at least one of a photovoltaic cell or a solar cell.

3. The sensing device of claim 1, wherein the optical communication device comprises a light-emitting diode (LED).

4. The sensing device of claim 1, wherein the optical communication device comprises a reflector.

5. The sensing device of claim 1, wherein the one or more sensors are powered by the power generated from the harvested light.

6. The sensing device of claim 1, wherein the optical communication device is powered by the power generated from the harvested light.

7. The sensing device of claim 1, wherein the optical communication device is configured to modulate the optical signal with the information about the one or more sensed biological features.

8. The sensing device of claim 1, wherein the optical signal comprises visible light.

9. The sensing device of claim 1, wherein the optical signal comprises infrared light.

10. The sensing device of claim 1, further comprising a transparent substrate that forms at least part of a body of the sensing device.

11. The sensing device of claim 10, wherein the photodetector is disposed on or within the transparent substrate.

12. The sensing device of claim 10, wherein the one or more sensors are disposed on or within the transparent substrate.

13. The sensing device of claim 10, wherein the optical communication device is disposed on or within the transparent substrate.

14. The sensing device of claim 1, further comprising a microprocessor.

15. The sensing device of claim 1, further comprising a memory.

16. A method, comprising:
sensing, by one or more sensors in a sensing device at an eye, one or more biological features associated with the eye;
harvesting, by a photodetector in the sensing device, ambient light to generate power for the sensing device; and
transmitting, by an optical communication device in the sensing device, an optical signal, wherein the optical signal communicates information about the one or more sensed biological features.

17. The method of claim 16, further comprising:
powering the one or more sensors by the power generated from the harvested light.

18. The method of claim 16, further comprising:
powering the optical communication device by the power generated from the harvested light.

19. The method of claim 16, further comprising:
modulating, by the optical communication device, the optical signal with the information about the one or more sensed biological features.

20. The method of claim 16, wherein the sensing device comprises a memory, further comprising:
storing the information about the one or more sensed biological features in the memory.

* * * * *